US008029785B2

(12) United States Patent
Schiltz et al.

(10) Patent No.: US 8,029,785 B2
(45) Date of Patent: Oct. 4, 2011

(54) THERAPEUTIC ANTIBODIES FOR TREATMENT AND PROPHYLAXIS OF TRANSMITTABLE VIRAL DISEASES

(75) Inventors: James M. Schiltz, Sisseton, SD (US); Marshall K. Brinton, Spicer, MN (US); James K. Petell, Grand Forks, ND (US); David S. Bradley, Grand Forks, ND (US)

(73) Assignee: Avianax, LLC, Grand Forks, ND (US)

(*) Notice: Subject to any disclaimer, the term of this patent is extended or adjusted under 35 U.S.C. 154(b) by 0 days.

(21) Appl. No.: 12/176,793

(22) Filed: Jul. 21, 2008

(65) Prior Publication Data

US 2008/0279863 A1 Nov. 13, 2008

Related U.S. Application Data

(63) Continuation of application No. 11/459,832, filed on Jul. 25, 2006, now abandoned.

(60) Provisional application No. 60/595,652, filed on Jul. 25, 2005.

(51) Int. Cl.
*A61K 39/395* (2006.01)
*A61K 39/42* (2006.01)

(52) U.S. Cl. ................ 424/130.1; 424/159.1; 424/161.1

(58) Field of Classification Search ........................ None
See application file for complete search history.

(56) References Cited

U.S. PATENT DOCUMENTS

| | | | | |
|---|---|---|---|---|
| 3,316,153 | A | | 4/1967 | Van Frank |
| 3,627,873 | A | | 12/1971 | Moyer |
| 3,962,421 | A | | 6/1976 | Neurath |
| 4,000,257 | A | | 12/1976 | Cano |
| 4,724,210 | A | | 2/1988 | Oka et al. |
| 4,748,018 | A | * | 5/1988 | Stolle et al. ................ 424/157.1 |
| 6,682,883 | B1 | | 1/2004 | Monath et al. |
| 2003/0211110 | A1 | | 11/2003 | Shimoni et al. |
| 2004/0009178 | A1 | | 1/2004 | Bowdish et al. |
| 2006/0057149 | A1 | | 3/2006 | Johnson et al. |
| 2006/0067940 | A1 | | 3/2006 | Diamond et al. |

FOREIGN PATENT DOCUMENTS

| | | | |
|---|---|---|---|
| DE | 19504755 | A1 | 8/1996 |
| EP | 152270 | | 8/1985 |
| EP | 1371665 | A1 | 12/2003 |
| EP | 1552848 | A1 | 7/2005 |
| WO | WO-2004/026339 | A1 | 4/2004 |
| WO | WO-2004/067035 | A1 | 8/2004 |

OTHER PUBLICATIONS

Banet-Noach C, Simanov L, Malkinson M. Avian Pathol. Oct. 2003;32(5):489-94.*
Srivastava et al. Neutralizing antibody responses to HIV: role in protective immunity and challenges for vaccine design. Expert Rev. Vaccines. 3(4) Suppl. 33-52 (2004).*
Cohen. Is an Effective HIV Vaccine Feasible. Science. vol. 30. p. 99 (2005).*
Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*
Huang et al. Recent development o therapeutics for chronic HCV infection. Antiviral Res 71 (2006) 351-362.*
Berzofsky et al. Progress on new vaccine strategies against chronic viral infections. J Clin Invest. Aug. 2004;114(4):450-62.*
Racanelli et al. Presentation of HCV antigens to naive CD8+T cells: why the where, when, what and how are important for virus control and infection outcome. Clin Immunol. Jul. 2007;124(1):5-12.*
Malkinson et al. The assay of golsing hepatitis virus and antibody by spermagglutination and spermagglutination-inhibition. Avian Pathology. vol. 3, No. 3,p. 201-204 (1974).*
Kris et al. Passive serum antibody causes temporary recovery from influenza virus infection of the nose, trachea and lung of nude mice. Immunology, 1988, 63, p. 349-353.*

Agrawal et al., "Human Immunoglobulin as a Treatment for West Nile Virus Infection", *Journal of Infectious Diseases,* 2003, pp. 1-4, vol. 188, No. 1, Chicago, IL, U.S.A.

Austin et al., "An Outbreak of West Nile Virus—Associated Disease in Domestic Geese (*Anser anser domesticus*) upon Initial Introduction to a Geographic Region, with Evidence of Bird to Bird Transmission," *Can. Vet. J.,* 2004, vol. 45, pp. 117-123.

Behn et al., "Use of Polyclonal Avian Antibodies" *Chicken Egg Yolk Antibodies, Production and Application,* 2001, pp. 108-210.

Ben-Nathan et al., "Prophylactic and Therapeutic Efficacy of Human Intravenous Immunoglobulin in Treating West Nile Virus Infection in Mice," *J Infect. Dis.,* 2003, vol. 188, pp. 5-12.

Carlander, "Avian IgY Antibody: *In Vitro* and *In Vivo,*" Acta Universitatis Upsaliensis, Comprehensive Summaries of Uppsala Dissertations from the Faculty of Medicine, Mar. 6, 2002 (published Ph.D. dissertation, Uppsala University).

Casadevall, "Passive Antibody Administration (Immediate Immunity) as a Specific Defense against Biological Weapons," *Emerging Infectious Diseases,* 2002, vol. 8(8), pp. 833-841.

Chung et al., "Antibodies against West Nile Virus Nonstructural Protein NS1 Prevent Lethal Infection through FC γ Receptor-Dependent and—Independent Mechanisms," *J. Virol.,* 2006, vol. 80(3), pp. 1340-1351.

Diamond et al., "A Critical Role for Induced IgM in the Protection against West Nile Virus Infection," *J Exp. Med.,* 2003, vol. 198(12), pp. 1853-1862.

Engle et al., "Antibody Prophylaxis and Therapy against West Nile Virus Infection in Wild-Type and Immunodeficient Mice," *J. Virol.,* 2003, vol. 77(24), pp. 12941-12949.

(Continued)

*Primary Examiner* — Zachariah Lucas
*Assistant Examiner* — Michelle S Horning
(74) *Attorney, Agent, or Firm* — Womble Carlyle Sandridge & Rice, PLLC

(57) ABSTRACT

The invention provides methods and compositions for the treatment and prevention of a transmittable disease in a subject, such as avians and mammals. The methods and compositions of the invention specifically make use of avian antibodies to the disease to be treated or prevented. Administration of such avian antibodies to a subject has been shown effective for reducing mortality in a population of subjects that are infected, or become infected, with the disease. The invention also provides kits useful for detecting the presence of transmittable diseases in subjects.

18 Claims, No Drawings

OTHER PUBLICATIONS

Gea-Banacloche et al., "West Nile Virus: Pathogenesis and Therapeutic Options," *Ann. Intern. Med.*, 2004, vol. 140(7), pp. 545-554.

Granwehr et al., "West Nile Virus: Where Are We Now?", *Lancet Infectious Diseases*, 2004, pp. 547-556, vol. 4, No. 9, U.S.A.

Haley et al., "The Role for Intravenous Immunoglobulin in the Treatment of West Nile Virus Encephalitis", 2003, pp. 88-90, vol. 37, No. 6, Bethesda, MD, U.S.A.

Jackson, "Therapy of West Nile Virus Infection," *Can. J. Neurol. Sci.*, 2004, vol. 31, pp. 131-134.

Samina et al., "An Inactivated West Nile Virus Vaccine for Domestic Geese—Efficacy Study and a Summary of 4 Years of Field Application," Vaccine, 2005, pp. 4955-4958, vol. 23, Issue 41.p.

Tesh et al., "Persistent West Nile Virus Infection in the Golden Hamster: Studies on Its Mechanism and Possible Implications for Other *Flavivirus* Infections," *J. Infect. Dis.*, 2005, vol. 192, pp. 287-295.

Throsby et al., "Isolation and Characterization of Human Monoclonal Antibodies from Individuals Infected with West Nile Virus," *J. Virol.*, 2006, vol. 80(14), pp. 6982-6992.

Weingartl et al., "Comparison of Assays for the Detection of West Nile Virus Antibodies in Chicken Serum," *Canadian Journal of Veterinary Research*, 2003, pp. 128-132, vol. 47, No. 2.

Xiao et al., "West Nile Virus Infection in the Golden Hamster (*Mesocricetus auratus*): A Model for West Nile Encephalitis," *Emerging Infectious Diseases*, 2001, vol. 7(4), pp. 714-721.

Yang et al., "Plaque Reduction Test: an Alternative Method to Assess Specific Antibody Response to pIII-Displayed Peptide of Filamentous Phage M13," *J. Immunol. Methods*, 2003, vol. 276, pp. 175-183.

* cited by examiner

THERAPEUTIC ANTIBODIES FOR TREATMENT AND PROPHYLAXIS OF TRANSMITTABLE VIRAL DISEASES

CROSS-REFERENCE TO RELATED APPLICATIONS

The present application is a continuation of U.S. patent application Ser. No. 11/459,832, filed Jul. 25, 2006, now abandoned, which claims priority to Provisional Patent Application Ser. No. 60/595,652, filed Jul. 25, 2005, both of which are incorporated herein by reference in their entirety.

FIELD OF THE INVENTION

The present invention is directed to compositions and the use thereof in the treatment and prevention of transmittable diseases, and particularly viral diseases. The compositions incorporate serum comprising avian antibodies against the transmittable disease, and the compositions can be used in a variety of subjects, including avians and mammals.

BACKGROUND

Previously known approaches to dealing with epidemiological outbreaks of transmittable clinical diseases have traditionally focused on three approaches: isolation of affected individuals; use of antimicrobial agents, and use of vaccinations. Antimicrobial agents have been used successfully for treatment once the pathogen has been identified; however, if the microorganism is resistant to the antimicrobial agent, there are limited or no options other than relying on the patient's own immune system for recovery or survival (in the case of life-threatening infections).

Individuals have been routinely protected by vaccinating, or immunizing, against an attenuated bacterial or viral strain where the vaccine has demonstrated good efficacy in prior tests. The underlying flaws of vaccinations are its safety, lack of protection against diverse strains causing the disease, availability of sufficient supplies of the vaccine, and most importantly, administration of the vaccine in sufficient time prior to infection to elicit an immune response in the patient against the pathogen. Unfortunately, in the event that the population is not vaccinated by the time an outbreak reaches epidemic proportions, a vaccination program that requires multiple injections over a significant period of time would have very limited effectiveness in protecting the population. In addition, individuals having impaired immunity (i.e., are immunodeficient) would be unable to generate an effective response. Moreover, given the high cost of a broad vaccination program, the general population has been vaccinated to only a limited number of pathogens. The rise of numerous emerging infectious diseases and the threat of bioterrorism acts have significantly elevated the susceptibility of large populations to a potentially epidemic disease outbreak.

Another approach, which has been referred to as "passive therapeutic immunity," to dealing with infection is the use of therapeutic antibodies for the treatment of pathogenic agents that are incurable by antimicrobial agents. Passive therapeutic immunity may also be used for individuals who have not been previously vaccinated. For example, the use of therapeutic antibodies has been reported with different degrees of protection against anthrax, biological toxins, brucellosis, Q fever, plague, smallpox, tularemia, viral encephalitides, and viral hemorrhagic fevers. Recent work has focused on the use of monoclonal antibodies, particularly because they can be produced in cell culture in large quantities once the hybridoma cell line is isolated. Alternatively, a recombinant mouse monoclonal antibody can be engineered with human sequences (generally referred to as a "humanized antibody") and produced in large quantities, albeit at expensive costs that may be prohibitory for broad use.

A severe drawback of the use of monoclonal antibodies is that they recognize only a single site or epitope on the microorganism, which is not as effective as polyclonal antibodies that recognize multiple sites. For example, previous testing using anthrax polyclonal sera containing antibodies to several sites demonstrated protective efficacy of the polyclonal antibodies. However, when the same test was performed using monoclonal antibodies, only one of four monoclonal antibodies tested conferred protection. Another limitation of monoclonal antibody treatment is that monoclonal antibodies offer limited protection to pathogens where the epitope is not conservatively maintained, such as a pathogen having numerous species or viral pathogens that prone to a higher mutation frequency.

West Nile Virus is a specific example of a disease where treatment after contacting the disease shows little efficacy. Specifically, it is recognized in the art that there is not yet any experimental evidence that therapy with immunoglobulin will improve survival or neurological outcome of experimental animals when this therapy is initiated after the development of the clinical neurological disease. Further, no studies, either prophylactic for protection or post-infection for therapy, have demonstrated effectiveness of immunoglobulin treatment in animals that become infected by natural transmission of West Nile Virus.

Published U.S. Patent Application 2003/0211110 to Shimoni et al. discloses that hyperimmune sera collected from humans was able to facilitate the recovery of two immunocompromised patients tested positive by West Nile Virus upon continuous treatment with antibody delivered intravenously. In a separate report by Jackson, Can. J. Neurol. Sci., 2004, however, a patient showed no beneficial effect upon similar treatment. It is therefore unclear whether the specified treatment alone was responsible for the recovery of the patients, and more so, if immunosuppression was a key factor required for treatment.

In light of the above, it is clear that further, more effective methods of treating and preventing infection, particularly by a transmittable viral disease, are needed. The present invention provides pharmaceutical compositions and methods of preparation and use thereof that are particularly beneficial for treating and preventing such infection.

SUMMARY OF THE INVENTION

The present invention relates to pharmaceutical compositions and methods thereof that are useful for treating and preventing infection in a subject by a transmittable viral disease. In particular embodiments, the compositions of the invention are specifically useful for reducing mortality in animals that become infected or are infected with a transmittable viral disease. In a preferred embodiment, the pharmaceutical compositions are effective against indigenous West Nile Virus. The methods of the invention generally comprise administering to a subject a composition according to the invention. In certain embodiments, the composition comprises serum, and preferably, polyclonal antibodies against a transmittable viral disease, such as West Nile Virus. Preferentially, the serum and antibodies are of high neutralization titer. The present invention also relates to the use of avian polyclonal antibodies for the detection of indigenous West Nile Virus in live animals, either symptomatic or non-symptomatic.

In one aspect, the present invention provides a method for treatment or prophylaxis of a transmittable viral disease in a subject. In certain embodiments, the method comprises administering to the subject an amount of a serum effective for treating or preventing the infection, wherein the serum comprises avian antibodies against the transmittable disease. In one particularly preferred embodiment, the avian antibodies are goose antibodies. Particularly, the treatment or prophylaxis can be evidenced by a reduction in mortality in a population affected by, or subject to infection by, the transmittable viral disease.

According to this aspect, the invention is particularly beneficial in that the method can be carried out such that the subject can be an avian subject or a mammalian subject. Moreover, the transmittable disease against which treatment or prevention is provided can be selected from a variety of diseases, particularly viral diseases. In a preferential embodiment, the viral disease for which treatment or prophylaxis is provided is West Nile Virus (WNV). According to another preferred embodiment, the viral disease for which treatment or prophylaxis if provided is an avian influenza.

The serum effective for treating or preventing infection can be obtained from a variety of sources and prepared using various techniques as would recognizable by one of skill in the art. In a particular embodiment, the serum comprises sera collected from an avian host, which can include geese, ducks, turkeys, ostriches, and chickens. In a preferred embodiment, the sera are collected from one or more avian hosts that have been infected by a naturally occurring strain of the transmittable disease. In another embodiment, the sera are collected from one or more avian hosts that have been infected by injection of a naturally occurring strain or attenuated strain of the viral transmittable disease. Accordingly, the serum preferentially comprises polyclonal antibodies. Generally, the serum is treated to substantially remove active forms of the transmittable disease present in the serum. The serum preferably includes avian antibodies in a high neutralization titer. In one embodiment, the neutralization titer of the avian antibodies in the serum is at least about 1:200. The serum can be administered to the subject by a variety of routes. For example, the serum can be administered by injection, inhalation, orally, and combinations thereof.

According to another aspect of the invention, there is provided a pharmaceutical composition. In one embodiment, the composition comprises a serum effective for treating or preventing infection in a subject by a transmittable viral disease, wherein the serum comprises avian antibodies against the transmittable disease. The pharmaceutical compositions of the invention are particularly useful in the methods of the invention, as described above. In a preferred embodiment, the pharmaceutical composition of the invention comprises goose antibodies.

In still another aspect according to the invention, there is provided a diagnostic kit useful for detecting the presence of a transmittable viral disease in a sample. In one embodiment, the kit comprises avian polyclonal antibodies capable of binding to antigens on the viral disease and a detector capable of detecting the avian polyclonal antibodies bound to the antigens. The kit according to the invention is particularly useful for detecting the presence of an indigenous viral disease. This is achieved in that the polyclonal antibodies used in the kit are preferably obtained from one or more avians that have been infected by a naturally occurring strain of the disease, such as WNV. Methods of detection include any and all forms of immunological detection that use serum, polyclonal antibodies, or antibody fragments as the binding part of the detection.

DETAILED DESCRIPTION OF THE INVENTION

The present inventions now will be described more fully hereinafter with reference to specific embodiments of the invention and particularly to the various drawing provided herewith. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In describing the present invention, various terms and phrases may be used herein, and such terms and phrases will have the same meaning thought the specification.

"Serum" means any fraction of blood serum that contains antibodies and one or more further protein blood components, said protein blood components comprising at least 30% by weight of the serum.

"Polyclonal antibodies" means a fraction of antibodies isolated from a host, the fraction comprising at least 80% of the total group of different antibodies produced by different immune cells in the host having affinity for different antigens on a virus.

"Neutralization titer" means quantification of an antibody that prevents or treats viral infection and subsequent detrimental viral effects, including cell death, in vitro, such as cell cultures including plaque assays, or in vivo, such as animal testing and clinical treatment. Antibodies that are shown present in a sample by ELISA, Western analyses, or like methods may or may not exhibit a neutralization titer.

"Natural transmission" means the transmission of an indigenous transmittable viral disease that occurs as a result of one or more animals being infected in an environment where the animal is freely exposed to carriers of the transmittable viral disease.

"Naturally occurring strain" or "indigenous strain" means a viral strain that is present in the natural environment and not having been reproduced in a laboratory.

"Attenuated" means a viral strain that has been weakened or made less virulent.

"Gosling" means any goose that has not reached maturity in terms of reaching a breeding age.

The treatment of human patients with of mammalian antibodies is known to cause strong immunoreactions in non-immunosuppressed human patients. The administration of horse antivenin can produce side effects in humans such as severe allergic reactions, and, in extreme cases, death. Therefore, in the ever-increasing need for effective treatment and prevention of disease, particularly viral disease, an alternative to mammalian antibodies is needed.

Avian antibodies are likely to have fewer side effects because they do not activate mammalian complement systems, bind to mammalian rheumatoid factors, naturally occurring anti-mammalian antibodies, or mammalian Fc receptors. Avian antibodies have been previously known for use in various method of treating humans, such as in the treatment of snakebites. However, prior to the present invention, it was unknown whether avian antibodies could be used to treat or prevent infection by a transmittable viral disease in other avians, and more preferably, mammals.

According to the present invention, it has been found that avian therapeutic antibodies can be an effective means to protect and treat a population of birds in the field by delivery of an effective dose of the therapeutic antibodies. Moreover, it has been found that avian therapeutic antibodies can also be an effective means to protect and treat mammals.

Therefore, according to various embodiments of the present invention, there are provided compositions and methods of use thereof for treating or preventing infection in a subject by a transmittable viral disease. The invention is particularly characterized by the realization of the therapeutic ability of high neutralization titer serum to a transmittable viral disease collected from animals that were naturally infected with the transmittable viral disease. Alternatively, high neutralization titer sera may be produced by immunization with an attenuated strain of a transmittable viral disease.

Treatment and prevention, according to the invention, are particularly evidenced by a reduction in the mortality rate in a population of subjects to which the serum is administered. Previous attempts to affect treatment of so-called "previously un-curable diseases" have been limited to alleviation or amelioration of symptom associated with the disease. Moreover, while such previous attempts have alleged prolonging the survival of infected subjects, such attempts have specifically failed to evidence actual reduction in the mortality of previously infected subjects. Even more particularly, there has been no evidence provided heretofore of any methods of preventing infection through use of avian antibodies and subsequently reducing mortality in a population at risk for infection by a transmittable viral disease. According to the present invention, there are provided methods of reducing mortality in a population of subjects by both treatment and prophylaxis through use of avian antibodies.

In addition to reducing mortality in a population of subjects, treatment according to the present invention can be understood to relate to lessening or complete cessation of one or more symptoms associated with the transmittable viral disease. Treatment can also include avoiding worsening of symptoms present at the time of first treatment and avoiding occurrence of further symptoms not present at the time of first treatment. Accordingly, in one embodiment, treatment can be effected through preventing or limiting one or more symptoms associated with infection by the transmittable viral disease.

Prevention of infection according to the present invention does not necessarily mean completely preventing a subject from contracting a transmittable viral disease. Rather, a subject could contract the disease after administration of the composition of the invention such that testing would indicate the presence of the virus in the subject, but the subject could be completely free of symptoms associated with the disease. In such a case, even though a subject could test positive for the disease, the absence of symptoms associated with the disease would indicate prevention. Accordingly, in one embodiment, the invention is directed to a method of preventing active infection in a subject. Prevention could also be evidenced by a reduction in mortality in a population of subjects to which the composition of the invention has been administered. In such a case, reduced mortality, when compared to a population not subject to administration of the inventive composition, would be indicative of prevention according to the invention. Preferably, prevention means complete absence of infection in a subject to which the composition of the invention has been administered.

In one embodiment, the present invention provides a pharmaceutical composition. The inventive composition, which is more particularly described in the various Examples provided herein, comprises a serum effective for treating or preventing infection in a subject by a transmittable disease. More particularly, the serum comprises avian antibodies against the transmittable disease.

The pharmaceutical composition of the invention is capable of use in the treatment or prevention of a variety of viral diseases. In one particular embodiment, the inventive composition is useful in the treatment or prevention of West Nile Virus. Accordingly, the composition may be more particularly described herein in reference to treating or preventing infection by West Nile Virus. Such further description, however, should not be viewed as limiting the scope of the present invention. Rather, the inventive pharmaceutical composition could be used in the treatment or prevention of infection by a variety of further viral diseases including, but not limited to, Hepatitis A, Hepatitis B, Hepatitis C, Human Immunodeficiency Virus, Respiratory Syncytial Virus, Cytomegalo Virus, Herpes Simplex Virus, Ectocarpus Siliculosus Virus, Vesicular Stomatital Virus, viral encephalitides (such as Eastern equine encephalomyelitis virus, Venezuelan equine encephalomyelitis virus, and Western equine encephalomyelitis virus), viral hemorrhagic fevers (such as Ebola, Marburg, Junin, Argentine, and Lassa), influenza viruses, and avian influenza viruses (sometimes called bird flu).

The serum used in the pharmaceutical composition of the invention can be obtained or prepared by a variety of methods, and the serum can include a variety of components. As previously noted, the serum comprises avian antibodies to the disease for which treatment or prevention is desired. The avian antibodies can be present naturally in the serum or can be incorporated into the serum as desired in the preparation of the serum.

In one preferred embodiment, the avian antibodies are naturally present in the serum as obtained from a host. Accordingly, it is preferred for the serum to comprise sera collected from one or more avian hosts. Preferably, the sera are collected from at least two avian hosts. In one particular embodiment, the avian host is a goose. Therefore, preparation of the inventive composition may be further described herein in reference to obtaining sera from geese, but such further description should not be viewed as limiting the scope of the invention. Rather, the host could comprise further avians including, but not limited to ducks, geese, turkeys, ostriches, chickens, and any further avians recognizable by one of skill in the art as being useful in light of the further disclosure provided herein.

Preferably, those avians of the biological family Anatidae, or commonly known as waterfowl, are preferred over other avian species. For example, the current highly pathogenic avian influenza (HPAI), H5N1, exhibits very high mortality, approaching or at 100%, to chickens and turkeys. In contrast, waterfowl birds are recognized as potential carriers of the H5N1 strain. Recent studies have shown various H5N1 strain variants cause substantially reduced or no mortality in domestic waterfowl relative that observed in chickens. The resistance of waterfowl is predicted to be due to the immunological system, and specifically antibodies, of the genus.

The avian hosts used for collecting the sera are preferentially avians that have been infected by a naturally occurring strain of the transmittable disease. Hosts having obtained a naturally occurring strain of the disease have been found to be particularly good sources of antibodies effective in the inventive composition described herein. The avian host can be a host that is actively infected or a host that has been previously infected but did not succumb to the disease.

The sera collected from the avian hosts can be used in its natural form or may be further processed or treated. For example, the sera are preferably treated to substantially remove active forms of the transmittable disease that may be present therein. In one embodiment, polyclonal antibodies are obtained from the serum. Such polyclonal antibodies may be used separate from the serum, used with a separate serum, or reintroduced into the same serum. The polyclonal antibodies can be isolated using a variety of procedures, including chromatography, ammonium sulfate separation, molecular selection protocols, or combinations thereof.

The serum used in the pharmaceutical composition of the invention preferably exhibits a high neutralization titer for the avian antibodies. In one preferred embodiment, the serum contains a high neutralization titer for goose antibodies. As used herein, a neutralization titer is understood to mean a degree of dilution at which a positive detection for a test component may still be found. Titer may be expressed in a variety of dilutions, and the use of a specific dilution in describing the present invention should not be viewed as limiting the invention. By describing the serum as comprising a high neutralization titer of avian antibodies, it is generally meant that the neutralization titer of the serum for the avian antibodies is higher that would be exhibited by the serum under normal conditions. According to one embodiment, normal conditions refers to conditions wherein the serum is obtained from a host that has not been infected with the disease for which antibodies are to be observed. According to another embodiment, the serum neutralization titer can be considered high titer if the neutralization titer is high than would be exhibited if the serum was obtained from a host infected with a non-naturally occurring strain of the disease against which antibodies are to be observed. In one specific embodiment, the neutralization titer of the serum is at least about 1:200. Preferably, the neutralization titer is even higher. For example, in certain embodiment, it is preferable for the neutralization titer of the serum for the avian antibodies to be at least about 1:500, at least about 1:1,000, at least about 1:2,000, at least about 1:3,000, or at least about 1:4,000. In certain embodiments, the neutralization titer for the serum is in the range of 1:320 to 1:8,192, in the range of 1:512 to 1:8,192, in the range of 1:1,024 to 1:8,192, or in the range of 1:2,048 to 1:4,096. Preferably, neutralization titer is evaluated in terms of polyclonal antibodies to the disease to be observed.

Serum neutralization titer for protective antibodies can be a critical factor in the effectiveness of a treatment or prophylactic prepared using the serum. Previous attempts to prepare formulations for treating West Nile Virus have centered on the use of the serum obtained from human hosts. For example, Ben-Nathan et al. (*J Infect Dis*. 2003; 188: 5-12) tested the efficacy of serum obtained from Israeli and U.S. human hosts. They determined that immunoglobulin G (IgG) preparations from Israeli donors had an anti-WNV antibody titer of 1:1600 when evaluated by ELISA. When evaluated by the plaque-reduction test, however, the antibody titer reported for the preparation was >1:80. Preparations made from U.S. blood donors were found to have a titer of only 1:10 when measured by ELISA. One description of a plaque-reduction test is provided by Yang et al., *Journal of Immunological Methods* 276, (2003):175-183, which is incorporated by reference in its entirety.

In light of these results, it was surprising, according to the present invention, to find that sera obtained from avian hosts exhibited significantly higher neutralization titers for protective antibodies than exhibited by sera obtained from human hosts. Accordingly, compositions and methods of the present invention, which incorporate particularly high neutralization titer sera, would be expected to much more useful for treating and preventing infection by viral diseases, such as West Nile Virus.

Serum having a high neutralization titer against an indigenous transmittable virus can be prepared according to a variety of methods. In one embodiment, such a method can comprise exposing one or more avian hosts in an open environment where the animals freely interact with a transmission host and with each other if a population is used. The preferred avian is one that is known to readily contract the transmittable virus of interest. The transmission host can be another avian capable of passing the disease on to host or can be a separate entity. For example, in the case of West Nile Virus, the transmission host is generally the mosquito. Testing has indicated that polyclonal antibodies can be particularly obtained from a population of avian hosts where at least 3% of the avians previously infected with the viral disease died, or in populations where the animals already showed high neutralization titer to the transmittable virus disease.

It has further been found that utilizing younger hosts for obtaining sera can be more effective, particularly for providing higher neutralization titer sera. For example, when geese are used as the host for obtaining the sera, obtaining sera from goslings rather than breeders has been found effective for obtaining sera with higher neutralization titers for protective antibodies.

The pharmaceutical composition of the invention can be used, according to the methods of the invention, in a variety of subjects. In one embodiment, the pharmaceutical composition is useful in treating or preventing infection by a transmittable viral disease in avian subjects. While such treatment or prevention may be with any avian subject, it is particularly useful with farm-raised avians, such as geese, ducks, turkeys, ostriches, and chickens. Likewise, in another embodiment, the pharmaceutical composition is useful in treating or preventing infection by a transmittable viral disease in mammalian subjects. Such mammalian subjects can particularly include humans. In further embodiments, the composition may be used in further mammalian subjects, such as goats, horses, rabbits, rats, mice, pigs, cat, dogs, and the like. In another preferred embodiment, any captive animal, such as exotic zoo animals, may be treated with the pharmaceutical composition prior or becoming infected with transmittable viral disease. In particular, the composition may be used in those animals where a vaccine is not economically feasible or has not been shown to provide protection.

In light of the above, it becomes particularly clear that the pharmaceutical composition of the invention is particularly useful in a method of treating or preventing infection in a subject by a transmittable viral disease. Accordingly, in certain embodiments, the present invention provides such methods. In one particular embodiment, the method comprises administering to the subject an amount of a serum effective for treating or preventing the infection, wherein the serum comprises avian antibodies against the disease.

Given the wide range of use associated with the above-noted methods, the administration of the serum can take on a variety of schedules. For example, the administration of the serum could be carried out prior to infection of the subject by the transmittable disease. Such a schedule would be particularly effective in the prevention of infection by the disease. In another embodiment, administration of the serum could be carried out at any point after infection of the subject by the disease. Such a schedule would be particularly effective as a treatment for the disease. When treatment is indicated, such as by evidence of symptoms common to the given disease, administration of the serum is preferably given until symptoms are no longer evident. One quantifiable symptom is the presence of virus neutralization titer levels in the sera corresponding to the viral transmittable disease. Preferably, the virus neutralization titer levels are reduced by 50% or more, and most preferably by 90%.

The serum may particularly be administered as part of a pharmaceutical composition. As such, the compositions of the present invention comprise serum, together with one or more pharmaceutically acceptable carriers therefore, and optionally, other therapeutic ingredients. By "pharmaceutically acceptable carrier" is intended a carrier that is conventionally used in the art to facilitate the storage, administration, and/or the healing effect of the agent. Carriers should be acceptable in that they are compatible with any other ingredients of the composition and not harmful to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Compositions of the present invention may include short-term, rapid-onset, rapid-offset, controlled release, sustained release, delayed release, and pulsatile release formulations, providing the compositions achieve administration of the serum as described herein. See *Remington's Pharmaceutical Sciences* ($18^{th}$ ed.; Mack Publishing Company, Eaton, Pa., 1990), herein incorporated by reference in its entirety.

Pharmaceutical compositions according to the present invention are suitable for various modes of delivery, including oral, parenteral (including intravenous, intramuscular, subcutaneous, intradermal, and transdermal), and inhalation. The most useful and/or beneficial mode of administration can vary, especially depending upon the condition of the recipient and the disease for which treatment or prevention is desired. In certain embodiment, administration can be by a combination of routes, for example, an initial oral dose followed by a schedule of injections.

The pharmaceutical compositions may be conveniently made available in a unit dosage form, whereby such compositions may be prepared by any of the methods generally known in the pharmaceutical arts. Generally speaking, such methods of preparation comprise combining (by various methods) an active agent, such as the serum comprising avian antibodies, with a suitable carrier or other adjuvant, which may consist of one or more ingredients. The combination of the active ingredient with the one or more adjuvants is then physically treated to present the composition in a suitable form for delivery (e.g. shaping into a tablet or forming an aqueous suspension).

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use.

It is contemplated that the serum comprising avian antibodies will be administered to a subject (i.e., an avian or a mammal, preferably a human) in therapeutically effective amounts. That is, in an amount sufficient to effect treatment of a subject already infected by a disease or effect prevention of infection of the subject by the disease. In specific embodiments, an effective amount can be an amount effective to reduce mortality in a population infected by or at risk of infection by the disease. The effective amount of the serum comprising avian antibodies would be expected to vary according to the classification (e.g., avian or mammalian), weight, sex, age, and medical history of the subject. Other factors which influence the effective amount may include, but are not limited to, the severity of the subject's condition, the specific viral disease being treated, and the stability of the serum. Methods to determine efficacy and dosage are known to those skilled in the art. See, for example, Isselbacher et al. (1996) *Harrison's Principles of Internal Medicine* 13 ed., 1814-1882, herein incorporated by reference.

In another embodiment of the invention, the pharmaceutical composition comprising the serum is administered intermittently. By "intermittent administration" is intended administration of a therapeutically effective dose of the serum, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the serum comprising the avian antibodies. The time period of discontinuance may be longer or shorter than the period of continuous sustained-release or daily administration. During the time period of discontinuance, the antibody level in the subject may fall substantially below the maximum level obtained during the treatment. The preferred length of the discontinuance period depends on the concentration of the effective dose and the form of pharmaceutical composition used. The discontinuance period can be at least 2 days, at least 4 days or at least 1 week. In other embodiments, the period of discontinuance is at least 1 month, 2 months, 3 months, 4 months or greater. When the pharmaceutical composition is used as a vaccine, administration of the serum can be effected through vaccination schedules that may be later determined most effective for achieving a maximum inoculation against a specific transmittable viral disease.

The present invention, in addition to the above useful aspects, also provides a diagnostic kit useful for detecting the presence of a transmittable viral disease in a sample. Generally, the sample will have been obtained from one or more subjects to determine the presence of an active or dormant infection in the subject by a given disease. In one embodiment, the diagnostic kit comprises avian polyclonal antibodies capable of binding to antigens on the viral disease and a detector capable of detecting avian polyclonal antibodies bound to the antigens.

The avian polyclonal antibodies used in the diagnostic kit can be obtained as otherwise described herein. It is particularly useful for the avian antibodies to comprise goose antibodies.

The detector used in the diagnostic kit of the invention can comprise any immunological detection means that use serum, polyclonal antibodies, or antibody fragments as the binding part of the detection. Examples of such methods which would be useful according to the invention include, but are not limited to, ELISA, immunolocalization using tagged antibodies, Western blots, Ouchterlony double diffusion, immunoprecipitation, strip tests, or the like.

EXPERIMENTATION

The present invention is more fully illustrated by the following examples, which are set forth to illustrate certain embodiments the present invention and are not to be construed as limiting.

Example 1

Preparation of High Neutralization Titer Serum for Viral Protective Bird Antibody Antibody titer measured by serum neutralization (SN) assays were performed to provide analyses of the protective capabilities of the goose antibody to viral infection over traditional ELISA assays that measure binding affinity to viral epitopes. Such traditional methods have shown discrepancies in the past. For example, in studies performed by Ben-Nathan et al. in obtaining antibodies from human subjects, the ELISA titer was reported to be 1:1600; however, the functional protective capabilities were shown to be substantially lower and were actually in the range of 1:80 to 1:320 (*J Infect Dis* 2003; 188: 5-12).

In the present study, geese of a variety of ages were exposed to West Nile Virus, sera were collected from the geese, and the sera of the infected geese were tested using a sera microtiter neutralization plaque assay to measure the usefulness of the sera for protecting cells from viral infection and death. Briefly, a serial 2-fold dilution of goose sera (up to a dilution of 1:8192) were prepared in 96-well microtiter plates and 50 ul PFU of West Nile Virus were added. After incubation at room temperature for 1 hr., $1 \times 10^4$ Vero cells were added to the mixtures to test for plaque reduction and were incubated for seven days. Plaque reduction neutralizing titers were expressed as the reciprocal of the highest dilution that gave 50% plaque reduction. Experiments indicated that goslings had a significantly higher titer for West Nile Virus antibodies than breeder stock geese, which are used for egg production. In fact, breeder stock geese exhibited a 4 fold lower titer for West Nile Virus antibodies than observed in the younger goslings.

Testing indicated that the sera obtained from the goslings exposed to West Nile Virus had a SN titer of over 4000 by 3 weeks after exposure. The neutralization titer peaked to over 8000 between 35 days to 70 days after exposure and decreased to about 1000 by 90 days after exposure to West Nile Virus. There was no evidence of reduced neutralization titer levels in the ages examined. Surprisingly, in contrast to reports of hyperimmune sera of adult human exposed to West Nile Virus, the neutralization titer of gosling sera was up to 100 fold higher than that observed in human sera (as evidenced by the Ben-Nathan et al. 2003 study referenced above). Accordingly, sera obtained from bird hosts infected with West Nile Virus proved to have much higher neutralization titer for protective antibodies than sera obtained from human hosts.

Actual measured neutralization titer levels in sera collected from goslings infected with West Nile Virus, as described above, are provided below in Table 1. The age of the bird at the time of infection with West Nile Virus and the neutralization titer level at a specified number of days post-infection are provided.

TABLE 1

| Days of Age | Titer Level | Days After Infection |
| --- | --- | --- |
| 127 | 4,096 | 21 |
| 128 | 4,096 | 22 |
| 128 | 4,096 | 22 |
| 120 | 4,096 | 25 |
| 132 | 4,096 | 26 |
| 120 | 4,096 | 26 |
| 123 | 4,096 | 26 |
| 125 | 4,096 | 28 |
| 126 | 4,096 | 29 |
| 135 | >8,192 | 30 |
| 127 | 4,096 | 30 |
| 124 | 4,096 | 30 |
| 132 | 4,096 | 32 |
| 133 | 4,096 | 33 |
| 134 | 4,096 | 33 |
| 128 | >8,192 | 34 |
| 132 | >8,192 | 39 |
| 128 | 4,096 | 40 |
| 127 | >8,192 | 46 |
| 125 | 4,096 | 51 |
| 123 | 4,096 | 52 |
| 133 | >8,192 | 52 |
| 134 | >8,192 | 53 |
| 127 | >8,192 | 53 |
| 133 | >8,192 | 54 |
| 141 | >8,192 | 60 |
| 127 | 4,096 | 64 |
| 127 | 4,096 | 65 |
| 133 | 4,096 | 66 |
| 130 | 4,096 | 66 |
| 134 | 4,096 | 67 |
| 126 | >8,192 | 68 |
| 126 | 4,096 | 68 |
| 127 | >8,192 | 69 |
| 121 | 2,048 | 69 |
| 127 | 4,096 | 69 |
| 125 | 2,048 | 73 |
| 132 | 4,096 | 73 |
| 120 | 4,096 | 75 |
| 125 | 2,048 | 75 |
| 120 | 4,096 | 76 |
| 126 | 4,096 | 76 |
| 126 | 2,048 | 76 |
| 126 | 2,048 | 76 |
| 103 | 4,096 | 76 |
| 133 | 4,096 | 77 |
| 135 | 4,096 | 77 |
| 127 | 4,096 | 77 |
| 128 | 4,096 | 77 |
| 125 | 4,096 | 78 |
| 140 | 4,096 | 81 |
| 125 | 4,096 | 82 |
| 144 | 4,096 | 84 |
| 125 | 4,096 | 84 |
| 113 | 2,048 | 84 |
| 126 | 4,096 | 85 |
| 114 | 2,048 | 85 |
| 126 | 4,096 | 86 |
| 117 | 1,024 | 88 |
| 117 | 2,048 | 88 |
| 120 | 2,048 | 88 |
| 126 | 1,024 | 90 |
| 114 | 1,024 | 94 |
| 114 | 1,024 | 94 |
| 153 | 1,024 | 95 |

Example 2

Evaluation of Goose Antiserum for Presence of West Nile Virus

Goose antiserum was examined for the presence of West Nile Virus RNA by RT-PCR analysis. DNA was amplified from the prepared RNA in a Perkin-Elmer Model 480 thermal cycler. Primers were designed to map the conserved sequences of the polyprotein gene (West Nile Virus Oligo Detect Kit, WNV Primer Mix [Part No. 5653], Chemicon International, California). The RT-PCR was performed with the QIAGEN one-step RT-PCR kit (QIAGEN, Valencia, Calif.) by using 5 µl of RNA and 0.3 µM of each primer in a 50 µl total reaction volume following the manufacture's protocol. When the PCR mixture was complete, the samples were overlaid with two drops of molecular biology grade mineral oil. All previous manipulations were performed in a Nuaire biological safety cabinet Model NU 425-400. The following cycling times and temperatures were used: cDNA synthesis; 50° C. for 30 minutes, 94° C. for 15 minutes followed by 40 cycles of 94° C. for 1 minute, 57° C. for 30 seconds and 72° C. for 1 minute followed by 72° C. for 15 minutes and 4° C. storage. Following PCR amplification of the DNA samples, the products were separated on 3% submerged agarose gels by electrophoresis. The separated products were visualized by staining with ethidium bromide and electronically photographed using UVP GDS8000 Gel Documentation System (Ultra Violet Products).

Goose antiserum was examined for the presence of West Nile Virus RNA by RT-PCR analysis performed using Chemicon West Nile Virus OLIGODETECT® on antiserum samples. RNA was isolated from goose antisera samples using the QIAamp Viral RNA kit (available from Qiagen) following its suggested protocol. The protocol utilized AVL/ carrier RNA addition to sera sample followed by application to a QIAamp spin column. After washing unbound material with AW2, the RNA was eluted using AVE buffer and collected by centrifugation. For RT-PCR analysis West Nile Primer Mix was added in suggested amounts to Qiagen One-Step RT-PCR Enzyme and sample, which included either RNA isolated from antisera or positive control West Nile Virus RNA included in kit. RT-PCR was performed as recommended by kit and subjected to agarose gel analysis.

The positive control West Nile Virus RNA sample exhibited the presence of the appropriate approximately 100 base pair PCR product, however no PCR products were observed in either the negative control or antisera samples. This observation ruled out potential artifacts caused by the presence of West Nile Virus particles in goose antiserum acting as a vaccine rather therapeutic agent.

Example 3

Purification of Goose Antibodies to West Nile Virus

Twenty liters of sera collected from geese infected with West Nile Virus was irradiated for 67 minutes/300 ml aliquots to eliminate any residual virus present in the sera, and the samples were examined by polymerase chain reaction (PCR) to ensure that the sera was virus free. The antibody fraction of the sera was purified by density centrifugation, dialyzed to remove gradient, and concentrated to approximately 3 times the original protein concentration. Purity of the goose antibody was established using RT-PCR analysis. All preparations were greater than 1:4000 determined by a microtiter plaque neutralization assay.

Example 4

Detection of West Nile Virus in Sick Birds Using VECTEST®

VECTEST® (Medical Analysis Systems) is recognized by the Center for Disease Control (CDC) as an effective rapid screening test for the detection of West Nile Virus. 39 geese exhibiting advanced West Nile Virus symptoms (e.g., lethargy, staggering, or blindness) were tested for the presence of the virus using VECTEST®. In this "on farm" use, only 5 geese of the 39 geese tested showed a positive VECTEST® response, ranging from +1 to +3 on the test scale. In contrast, the majority of tested geese were found to be positive for West Nile Virus when tested using RT-PCR. Within 7 days, all 5 of the birds testing positive by the VECTEST® died; however, 19 of the 34 birds testing negative by the VECTEST® died within the same period. Accordingly, VECTEST® analyses of serum failed to detect a positive response in most of the birds tested according to the kit instructions.

The brains of selected geese were examined for the presence of West Nile Virus and confirmed to be positive by histopathology for WNV lesions and by molecular PCR diagnostics by the Veterinary Diagnostic Laboratory at the University of Minnesota. The VECTEST® is a monoclonal antibody test based on a Saint Louis Encephalitis antigen panel and appears not to be sufficiently reactive to indigenous West Nile Virus. In contrast, the goose polyclonal antibodies reacted strongly to the indigenous West Nile Virus antigens present in the indigenous population and unexpectedly offer higher reactivity than the monoclonal antibodies used in the VECTEST®.

Example 5

Mortality Rate of Avians Treated with Antiserum Prior to Onset of West Nile Virus Disease Prior to any evidence of increased mortality due to natural infection by West Nile Virus, 6-10 week old goslings were treated by a single subcutaneous injection of 3 milliliters goose antisera according to the invention per gosling. The antisera was negative for West Nile Virus RNA and had a neutralization titer of $\geq 1:2,000$. The antisera treated group included 4705 males and 5095 females. As a control, an untreated group including 5462 males and 7536 females was also evaluated. All animals were continuously exposed to natural infection by the West Nile Virus throughout the course of a six week period.

Deaths among the birds injected with the antisera and the control group was recorded over a 19 day period beginning one day after immunization when the mortality rates became elevated in control group. The percent mortality rates were calculated after first subtracting the average background mortality rate observed in periods when West Nile Virus outbreak was not observed. The percent mortality rate for treated and untreated female and male birds is shown below in Table 2. The overall mortality rate decreased by approximately 60% to 80% in those goslings treated with antiserum. This results show that injection of antiserum can provide an effective control for reducing mortality rates due to West Nile Virus when given prior to onset of a natural outbreak of the disease in a population. RT-PCR analysis of the antiserum for West Nile Virus RNA indicated antibodies residing in the antiserum were effective agents in reducing mortality.

TABLE 2

| Gender | % Mortality in Untreated | % Mortality in Treated | % Reduced Mortality Rate |
| --- | --- | --- | --- |
| Male | 5.46 | 1.34 | 75% |
| Female | 2.56 | 1.10 | 57% |

Example 6

Mortality Rate after Onset of West Nile Virus Disease of Avians Treated with Antiserum In another study, goslings showing signs of West Nile Virus infection as judged by a higher mortality were given a single injection subcutaneously with 3 milliliters of goose antisera. The antisera was negative was West Nile Virus RNA and had a neutralization titer level ≧1:2000. The antisera treated group included 2463 males and 2379 females and an untreated control group included 5256 males and 7419 females. Deaths among the injected goslings and the control group were recorded over a 13 day period after the start of injection (such period corresponding to a period when mortality rates were elevated). The percent mortality rates were calculated after first subtracting the average background mortality rate observed in periods when West Nile Virus outbreak was not observed. The percent mortality rate for treated and untreated female and male birds is provided below in Table 3. The overall mortality rate in goslings treated with antiserum was decreased by 57% to 68%. These results show that injection of antiserum, and specific antibodies therein, provided an effective treatment for reducing mortality rates due to West Nile Virus after the natural outbreak of the disease in a population.

TABLE 3

| Gender | % Mortality in Untreated | % Mortality in Treated | % Reduced Mortality Rate |
|---|---|---|---|
| Male | 3.52 | 1.50 | 57% |
| Female | 3.94 | 1.26 | 68% |

Example 7

Evaluation of Prophylaxis Against West Nile Virus in a Large Population of Geese Via Administration of Therapeutic Antibodies to a Subset of the Population It is unclear whether in a goose flock affected by West Nile Virus the disease is spread by transmission via animal to animal in addition to naturally transmission by the original host (i.e., mosquitoes). A study was preformed to determine if the treatment of a sufficient segment of animal population is effective to prevent the spread of the disease within a large population of the entire flock, by potentially either reducing the transmission via animal to animal or reducing the viral pool for mosquitoes. Two sites (approximately 10 miles apart) were selected for testing, both sites being known to have previously had a similar mortality rate in geese due to natural infection by West Nile Virus. At site 1, no geese were treated. At site 2, approximately 65% of the geese were treated with goose sera or antibodies.

WNV was observed at site 1 approximately 10 days prior to first observance at site 2. At site 1, the mortality rate associated with West Nile Virus infection was approximately 13.5% of the population over 25 days. In contrast, at site 2, in antibody treated geese, the mortality rate was 1.56% over the same day period corresponding to an 8 fold decrease in mortality relative to site 1. Surprisingly, in 35% of the geese at site 2 that were not injected with sera, the mortality was also substantially decreased relative to site 1; nevertheless, the mortality rate in untreated geese at site 2 was still higher than those treated with the antibody. This suggests a benefit to untreated animals in a larger population arising from treatment of a subset of the population. Results are shown in Table 4.

TABLE 4

| Treatment | Farm Site | Mortality % | Fold Reduction in Mortality |
|---|---|---|---|
| Untreated | 1 | 13.58% | — |
| Antiserum Treated | 2 | 1.56% | 8.70 |
| Untreated | 2 | 3.02% | 4.39 |

Example 8

Toxicity and Longevity Studies in Mammals of Goose Antibodies to West Nile Virus Ten young adult mice were injected intramuscularly with 0.2 ml purified goose antibodies to West Nile Virus, 10 separate young adult mice were injected intramuscularly with 0.4 ml purified goose anti-WNV antibodies, and 10 separate age-matched control mice were injected intramuscularly with saline. All mice were observed for the first 24 hours and daily for 3 weeks for adverse clinical symptoms including changes in food and water consumption, wasting, and grooming. Neither acute nor chronic symptoms were detected in any of the antibody treated mice.

At 3 weeks post-injection, all 30 of the mice were euthanized and examined for gross anatomical changes with none detected. All spleens and livers were removed and analyzed histologically. No inflammation was noted in any of the experimental mice, and no difference was detected between the antibody treated and control mice. There was no indication that there was any adverse reaction with the introduction of goose antibodies into the mice.

Example 9

Efficacy of Goose Antibodies Against West Nile Virus in Hamsters

To determine if goose antibodies to West Nile Virus would be effective in mammals, the golden hamster model of WNV infection was utilized. The golden hamster model is discussed by Tesh et al., Persistent West Nile Virus Infection in the Golden Hamster: Studins on its Mechanism and Possible Implications for Other Flavivirus Infections, *The Journal of Infectious Diseases* (2005), 192:287-295, and Xiao et al., West Nile Virus Infection in the Golden Hamster (*Mesocricetus auratus*): a Model for West Nile Encephalitis, Emerging Infectious Diseases (2001), 7(4):714-721, both of which are incorporated herein by reference in their entirety.

In the present test, ten hamsters were injected with purified goose antibodies to West Nile Virus, and 10 control hamsters received saline (the day of injection being day 0). On day 1 all 20 hamsters were infected with $10^{3.2}$ PFU (plaque forming units) of WNV-Iowa strain.

The antibody-treated group and the saline group each divided into two groups of five hamsters, the groups being orbitally bled either on days 1 and 3 or days 2 and 4. WNV neutralization titer was determined in 1:5 dilutions of sera. WNV was detectable in the control group by day 1 and increased until the third day when the neutralization titer leveled off (see Table 5 below). Eight of the 10 hamsters from the saline group showed a positive WNV neutralization titer at the level tested. In contrast to the saline treated animals, none of the hamsters receiving the goose antibodies showed any functional virus at the lowest dilution, $10^{-1}$.

TABLE 5

| Study Group | Average WNV-Ia Titer/mL | | | |
|---|---|---|---|---|
| | Day 1 | Day 2 | Day 3 | Day 4 |
| Saline Group | | | | |
| Group 1 | $2.01 \times 10^2$ | | $1.67 \times 10^5$ | |
| Group 2 | | $3.34 \times 10^4$ | | $9.19 \times 10^4$ |
| Antibody Treated | | | | |
| Group 1 | ND | | ND | |
| Group 2 | | ND | | ND |

ND—Not Detected

To detect long term effects of the viral infection beyond the four-day test described above, the hamsters were monitored for the next 11 days for clinical signs of West Nile Virus, including lethargy, wasting, and death. The hamsters receiving only saline showed 60% overall mortality over days 4 through 11. Mortality was evidenced by natural death or euthanization in light of viral effects. Complete mortality rates for both groups are shown below in Table 6.

TABLE 6

| Study Group | Died or Euthanized |
|---|---|
| Saline Group | |
| Group 1 | 2/5 |
| Group 2 | 4/5 |
| Antibody Treated | |
| Group 1 | 0/5 |
| Group 2 | 0/5 |

As evidenced by the results provided in Table 5 and Table 6, goose antibodies were shown effective for preventing infection by West Nile Virus in mammals.

Example 10

Preparation of High Neutralization Titer Serum Against Avian Influenza

To test production of therapeutic antibody to avian influenza, an avian influenza virus strain was produced in eggs as a vaccine stock. A stock sample of H3N2 was obtained from ATCC (VR-777) culture collection and used as a viral stock for injection into waterfowl eggs. Two lines, P2SM and JMOP, of goose embryos were used for virus production. Goose embryos at 11 to 17 days of incubation were candled for viability prior to viral injection. Holes were drilled at positions on egg that provided access to either the air sac or chorioallantoic membranes. Approximately 10 to 100 ul of virus stock solution was placed in the air sac or injected into the chorioallantoic membrane. The hole was sealed using glue and returned in the upright position into an incubator. The eggs were monitored for viability by candling.

After 3 to 6 days, approximately 0.5-1.0 ml of allantoic fluid were collected from the allantoic cavity of the goose embryos. RNA was extracted from the samples and analyzed according to the protocol recommended in the RT-PCR kit (available from Qiagen) used for detection of H3N2 virus. Briefly, 500 ul of allantoic fluid were mixed with 500 ul of RLT buffer. From this, 700 ul was applied to a RNeasy column and microfuged for 15 sec and repeated with the remaining sample. 700 ul of Buffer RW1 was applied and the column was microfuged for 15 sec. Next, 500 ul of RPE was similarly applied and microfuged and repeated. To elute bound RNA, 30 to 50 ul of RNase free water was added and microfuged for 15 sec and the sample collected for RT-PCR.

RT-PCR was performed using H3N2 primers obtained from Integrated DNA Technologies, Inc. (Coralville, Iowa). The primer set included a forward primer, M2F, and a reverse primer, M253R. RT PCR was performed according to the Influenza A virus protocol by Fouchier et al. (*J. Clin. Microbiology* 38, 2000), which is incorporated herein by reference. Briefly, RT-PCR conditions were maintained for 30 min at 42° C. and 4 min at 95° C. followed by 40 cycles of 1 min at 95° C., 1 min at 45° C. and 3 min at 72° C. Approximately 15 ul of nucleotide sample was added to a reaction containing 5 ul of each primer and mixed with RT-PCR buffer containing TAQ enzyme and dNTP. Samples of RT-PCR were analyzed by agarose electrophoresis and ethidium bromide staining.

In control eggs (mock injected, or eggs injected with virus but harvested after 3 hours), no virus was detected by the RT-PCR. In contrast, H3N2 virus was found to be produced in 8 of 10 goose embryos. Embryos of both goose strains were shown to produce virus. Highest virus production was exhibited upon injection into the allantoic sac compared to the air sac.

In the event that multiple strains of the transmittable virus are present, two or more strains can be inoculated individually into resistant avian embryos and the allantoic are pooled to provide broader protection to strain variants. For common influenza vaccine typically three predominant strains from the past and/or during the present year are used. After the allantoic fluids are pooled, a number of methods have been used to simplify the recovery of the virus or viral products from the allantoic fluids. Examples of such methods can be found in the following, all of which are incorporated by reference herein: U.S. Pat. No. 3,627,873; U.S. Pat. No. 4,000,527; U.S. Pat. No. 3,316,153; U.S. Pat. No. 4,724,210; and U.S. Pat. No. 3,962,421.

The isolated H3N2 influenza viral particles are attenuated by a number of methods to those skilled in the art that inactivate the viral nucleic acid or disrupt key viral coat elements critical in viral infection or a combination of methods. The attenuated viral particles are injected one or more times into goslings for a period sufficient to produce an immune response, typically 3 to 10 weeks. The sera are then harvested from the animals and the sera are tested using a sera microtiter neutralization plaque assay to measure their usefulness in protecting Vero cells from viral infection. Upon demonstrating high neutralization titer goose sera, antibodies are isolated from sera by density centrifugation. The antibodies are dialyzed to remove gradient and are concentrated to approximately 3 times the original protein concentration.

The goose purified antibodies to avian influenza are tested in animals and are found to be effective for preventing infection or preventing or limiting one or more symptoms associated with infection by avian influenza.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating a mammal comprising administering to the mammal an amount of a composition comprising polyclonal goose antibodies against a transmittable viral disease, wherein the goose antibodies are not administered to the mammal prior to administering the composition.

2. A method of treating a mammal infected with a transmittable viral disease, the method comprising administering to the mammal after infection an amount of a serum comprising polyclonal goose antibodies against the transmittable viral disease, wherein the serum exhibits a neutralization titer of at least about 1:500 when evaluated according to a plaque reduction test, wherein the transmittable virus is West Nile Virus and wherein the goose antibodies are not administered to the mammal prior to administering the serum.

3. A method of treating a mammal comprising administering to the mammal an amount of a serum comprising polyclonal goose antibodies against a transmittable viral disease, wherein the antibodies are from a goose that has been infected by a naturally occurring strain of the transmittable viral disease such that the serum exhibits a neutralization titer of at least about 1:500 when evaluated according to a plaque reduction test, wherein the transmittable virus is West Nile Virus and wherein the goose antibodies are not administered to the mammal prior to administering the serum.

4. A method of treating a mammal comprising administering to the mammal an amount of a serum comprising polyclonal goose antibodies against a transmittable viral disease, wherein the serum exhibits a neutralization titer of at least about 1:2000 when evaluated according to a plaque reduction test, wherein the transmittable virus is West Nile Virus and wherein the goose antibodies are not administered to the mammal prior to administering the serum.

5. The method of claim 1, wherein the mammal is selected from the group consisting of goats, horses, rabbits, rats, mice, pigs, and humans.

6. The method of claim 1, wherein said treating comprises administering the composition to a mammal that is infected with the transmittable viral disease.

7. The method of claim 1, wherein the antibodies are from a goose that has been infected by a naturally occurring strain of the transmittable viral disease.

8. The method of claim 1, wherein said administering comprises a route of administration selected from the group consisting of injection, inhalation, oral administration, and combinations thereof.

9. The method of claim 1, wherein the transmittable viral disease is selected from the group consisting of West Nile Virus, Hepatitis B, influenza viruses, and avian influenza viruses.

10. The method of claim 1, wherein the transmittable viral disease is Hepatitis B.

11. The method of claim 1, wherein the transmittable viral disease is West Nile Virus.

12. The method of claim 1, wherein the transmittable viral disease is an influenza virus.

13. The method of claim 1, wherein the transmittable viral disease is an avian influenza virus.

14. The method of claim 9, wherein said treating comprises preventing infection in the mammal by the transmittable viral disease.

15. The method of claim 9, wherein said treating comprises preventing or limiting one or more symptoms associated with infection by the transmittable viral disease.

16. The method of claim 11, wherein the polyclonal goose antibodies are from a serum that exhibits a neutralization titer of at least about 1:200 when evaluated according to a plaque reduction test.

17. The method of claim 16, wherein the polyclonal goose antibodies are from a serum that exhibits a neutralization titer of at least about 1:500 when evaluated according to a plaque reduction test.

18. The method of claim 16, wherein the polyclonal goose antibodies are from a serum that exhibits a neutralization titer of at least about 1:1000 when evaluated according to a plaque reduction test.

* * * * *